US011460416B2

(12) United States Patent
Alvarez et al.

(10) Patent No.: US 11,460,416 B2
(45) Date of Patent: Oct. 4, 2022

(54) METHOD FOR MEASURING OIL IN WATER USING MULTI-FREQUENCY MICROWAVE MEASUREMENTS

(71) Applicant: SAUDI ARABIAN OIL COMPANY, Dhahran (SA)

(72) Inventors: Jose Oliverio Alvarez, Houston, TX (US); David Joseph Jacobi, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 155 days.

(21) Appl. No.: 17/039,892

(22) Filed: Sep. 30, 2020

(65) Prior Publication Data

US 2022/0099597 A1 Mar. 31, 2022

(51) Int. Cl.
*G01N 22/00* (2006.01)
*G01N 33/18* (2006.01)
(Continued)

(52) U.S. Cl.
CPC ......... *G01N 22/00* (2013.01); *G01N 33/1833* (2013.01); *G01N 33/2823* (2013.01); *G01N 1/42* (2013.01)

(58) Field of Classification Search
CPC . G01N 22/00; G01N 33/1833; G01N 33/2823
(Continued)

(56) References Cited

U.S. PATENT DOCUMENTS 4,862,060 A 8/1989 Scott et al.
6,147,503 A * 11/2000 Nelson ................... G01N 22/04
324/637
(Continued)

FOREIGN PATENT DOCUMENTS

JP 2008116385 A * 5/2008
WO 2003100393 A1 12/2003
(Continued)

OTHER PUBLICATIONS

Alvarez, et al., Dielectric Characterization of Geochemical Properties of Crude Oils and Gas Condensate at 25° C., in Proc. International Geoscience and Remote Sensing Symposium (IGARSS), Jul. 2017, Fort Worth, TX, USA. pp. 365-368.
(Continued)

*Primary Examiner* — Nathaniel J Kolb
(74) *Attorney, Agent, or Firm* — Bracewell LLP; Constance G. Rhebergen; Linda L. Morgan

(57) ABSTRACT

Embodiments of the disclosure provide a method of determining the presence of a hydrocarbon in an aqueous medium used for secondary oil recovery. The method includes the step of introducing the aqueous medium into a subterranean hydrocarbon formation to displace hydrocarbons. The method includes the step of retrieving an aqueous sample from the aqueous medium introduced into the subterranean hydrocarbon formation. The method includes the step of cooling the aqueous sample such that the aqueous sample is in a solid state. The method includes the step of exposing the aqueous sample to an electromagnetic wave at a microwave frequency such that a scattering response is induced from the hydrocarbon included in the aqueous sample. The method includes the step of determining permittivity of the hydrocarbon based on the scattering response.

12 Claims, 5 Drawing Sheets

(51) Int. Cl.
*G01N 33/28* (2006.01)
*G01N 1/42* (2006.01)

(58) Field of Classification Search
USPC .................................. 73/61.44, 61.41, 61.43
See application file for complete search history.

(56) References Cited

U.S. PATENT DOCUMENTS

| | | | |
|---|---|---|---|
| 7,587,290 | B2 | 9/2009 | Scott |
| 8,364,419 | B2 | 1/2013 | Potyrailo et al. |
| 8,513,311 | B2 | 8/2013 | Sagalowicz et al. |
| 8,653,819 | B2 | 2/2014 | Barmatz et al. |
| 9,255,475 | B2 | 2/2016 | Zuo et al. |
| 9,341,571 | B2 | 5/2016 | Mackay et al. |
| 9,526,692 | B2 | 12/2016 | Rehage |
| 9,585,837 | B2 | 3/2017 | Mai et al. |
| 9,958,570 | B2 | 5/2018 | Pearl et al. |
| 2008/0303534 | A1 | 12/2008 | Wee |
| 2019/0025275 | A1 | 1/2019 | Alvarez et al. |
| 2019/0120992 | A1 | 4/2019 | Stove et al. |

FOREIGN PATENT DOCUMENTS

| | | | |
|---|---|---|---|
| WO | 2016195113 | A1 | 12/2016 |
| WO | 2018154382 | A1 | 8/2018 |

OTHER PUBLICATIONS

Alvarez, et al., Permittivity Spectrum of Low-Loss Liquid and Powder Geomaterials Using Multipoint Re-entrant Cavities. IEEE Trans. Geosci. Remote Sens. 2019. DOI: 10.1109/TGRS.2019.2948052, pp. 1-16.

Balsamo, et al., Chemical Demulsification of Model Water-in-Oil Emulsions with Low Water Content by Means of Ionic Liquids, Brzilian Jounal of Chemical Engineering, vol. 34, No. 01, pp. 273-282, Jan.-Mar. 2017.

Fortuny,et al., Effect of Salinity, Temperature, Water Content, and pH on the Microwave Demulsification of Crude Oil Emulsions, Energy & Fuels 2007, 21, pp. 1358-1364.

Vallejo-Cardona,et al., Demulsification of Crude Oil-in-Water Emulsions by Means of Fungal Spores, Research Article, PLOS|ONE, DOI:10.1371/journal.pone.0170985, Feb. 24, 2017, pp. 1-17.

International Search Report and Written Opinion for International Application No. PCT/US2021/052283, report mail date Dec. 20, 2021; pp. 1-15.

Neusitzer, Thomas David; "On the Dielectric Properties and Normalized Radar Cross-Section of Crude Oil-Contaminated Sea Ice" Thesis submitted to the University of Manitoba Department of Electrical and Computer Engineering, 2017; pp. 1-139.

\* cited by examiner

METHOD FOR MEASURING OIL IN WATER USING MULTI-FREQUENCY MICROWAVE MEASUREMENTS

BACKGROUND

Field of the Disclosure

Embodiments of the disclosure generally relate to geochemical analysis of fluids. More specifically, embodiments of the disclosure relate to method for detecting and quantifying trace quantities of hydrocarbons present in an aqueous medium using microwave measurements.

Description of the Related Art

Water (including brine) is frequently used as a medium for secondary oil recovery. Water is injected into the subterranean hydrocarbon formation through injection wells to sweep hydrocarbons located in the formation. Secondary oil recovery reaches its limit when the injected water is produced in considerable quantities from the production wells or the production is no longer economical, or both.

Dielectric spectroscopy of geomaterials requires the knowledge of the dielectric properties of each component of the matrix. These components include fluids in the pores. Naturally, emphasis is given to the presence of water, the fluid with the greatest permittivity. Its greater dielectric constant, as compared to other fluids from the reservoir rock pores, allows for easier determination of the presence of water in the hydrocarbons, which is a major factor in determining economic life of a well.

Applications of dielectric properties of reservoir fluids have until recently focused mainly in water cut metering or on-line water determination. These applications require reliable estimates of the real part of the complex permittivity in order to use mixing models with the complex permittivity values for the emulsion. With the arrival of production from unconventional reservoirs, the interest in the low-loss fluids has increased.

SUMMARY

Embodiments of the disclosure generally relate to geochemical analysis of fluids. More specifically, embodiments of the disclosure relate to method for detecting and quantifying trace quantities of hydrocarbons present in an aqueous medium using microwave measurements.

Microwave measurements are useful for confirming the properties of the produced fluids and monitoring for changes that can occur during production. In order to obtain the most accurate complex permittivity values for low-loss fluids (such as hydrocarbons), microwave resonant cavities are implemented. To reduce the loss of broadband and to avoid the use of many cavities, embodiments of the disclosure provide the use of multipoint resonant cavities for application in the geosciences. Advantageously, hydrocarbons can be detected in saturated pore spaces that were previously subjected to water flooding. Advantageously, embodiments of the disclosure provide means to understand the efficiency of recovering hydrocarbons using water flooding methods during secondary oil recovery.

Embodiments of the disclosure provide methods to identify trace quantities of a nonconductive component (that is, hydrocarbons) within a conductive one (that is, an aqueous medium). Despite that water is not a low-loss fluid and does not resonate, an aqueous sample having trace quantities of hydrocarbons can be transformed to a solid state and subjected to a microwave resonant cavity to determine the presence of the hydrocarbons.

Embodiments of the disclosure provide a method of determining the presence of a hydrocarbon in an aqueous medium used for secondary oil recovery. The method includes the step of introducing the aqueous medium into a subterranean hydrocarbon formation to displace hydrocarbons. The method includes the step of retrieving an aqueous sample from the aqueous medium introduced into the subterranean hydrocarbon formation. The method includes the step of cooling the aqueous sample such that the aqueous sample is in a solid state. The method includes the step of exposing the aqueous sample to an electromagnetic wave at a microwave frequency such that a scattering response is induced from the hydrocarbon included in the aqueous sample. The method includes the step of determining permittivity of the hydrocarbon based on the scattering response.

In some embodiments, the method further includes the step of identifying hydrocarbon content of the aqueous sample. In some embodiments, the hydrocarbon content ranges between 0.001 wt. % and 10 wt. %. In some embodiments, the method further includes the step of obtaining a baseline measurement of the aqueous medium to be introduced into the subterranean hydrocarbon formation. In some embodiments, the retrieving step is conducted at a production well. In some embodiments, the aqueous sample has a temperature ranging between −50 deg. C. and 0 deg. C. in the cooling step. In some embodiments, the exposing step is conducted in a microwave resonant cavity. In some embodiments, the microwave resonant cavity provides at least four microwave frequencies. In some embodiments, the microwave frequency ranges between 100 MHz and 150 GHz. In some embodiments, the aqueous medium has a salinity ranging between 0.001 moles per liter (M/L) and 1 M/L. In some embodiments, the exposing step and the determining step are conducted using a vector network analyzer (VNA) or a reflectometer. In some embodiments, the determining step includes obtaining an $S_{11}$ reflection coefficient from the scattering response.

Embodiments of the disclosure also provide a method of determining the presence of a hydrocarbon in a high-loss fluid. The method includes the step of cooling the high-loss fluid such that the high-loss fluid is in a solid state. The method includes the step of exposing the high-loss fluid to an electromagnetic wave at a microwave frequency such that a scattering response is induced from the hydrocarbon included in the high-loss fluid. The method includes the step of determining permittivity of the hydrocarbon based on the scattering response.

In some embodiments, the method further includes the step of identifying hydrocarbon content included in the high-loss fluid. In some embodiments, the hydrocarbon content ranges between 0.001 wt. % and 10 wt. %. In some embodiments, the method further includes the step of obtaining a baseline measurement of the high-loss fluid in the absence of the hydrocarbon. In some embodiments, the high-loss fluid has a temperature ranging between −50 deg. C. and 0 deg. C. in the cooling step. In some embodiments, the exposing step is conducted in a microwave resonant cavity. In some embodiments, the microwave resonant cavity provides at least four microwave frequencies. In some embodiments, the microwave frequency ranges between 100 MHz and 150 GHz. In some embodiments, the high-loss fluid has a salinity ranging between 0.001 M/L and 1 M/L. In some embodiments, the exposing step and the determining step are conducted using a VNA or a reflectometer. In some embodiments, the determining step includes obtaining an $S_{11}$ reflection coefficient from the scattering response.

BRIEF DESCRIPTION OF THE DRAWINGS

So that the manner in which the previously-recited features, aspects, and advantages of the embodiments of this disclosure as well as others that will become apparent are attained and can be understood in detail, a more particular description of the disclosure briefly summarized previously may be had by reference to the embodiments that are illustrated in the drawings that form a part of this specification. However, it is to be noted that the appended drawings illustrate only certain embodiments of the disclosure and are not to be considered limiting of the disclosure's scope as the disclosure may admit to other equally effective embodiments.

Figure 1:
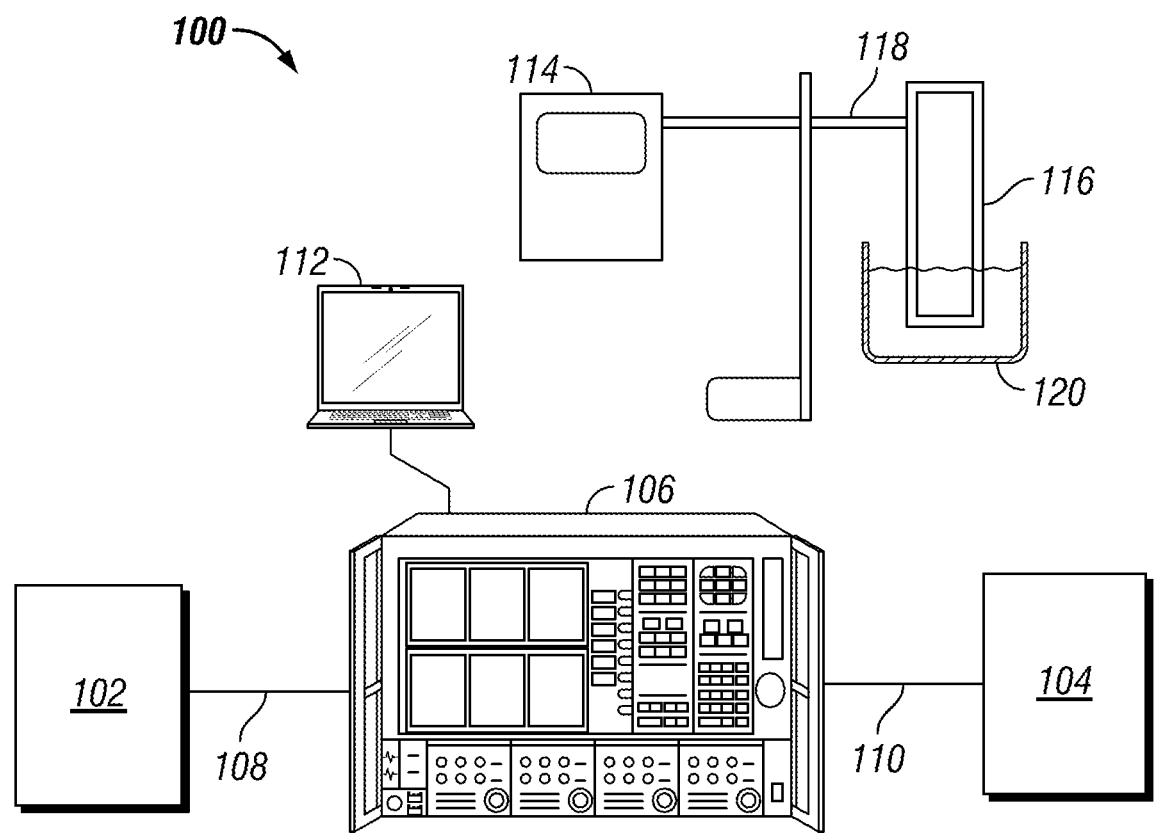
FIG. 1 is a schematic view of an example experimental setup for identifying trace quantities of hydrocarbons present in an aqueous medium, according to an embodiment of the disclosure.

In the accompanying Figures, similar components or features, or both, may have a similar reference label.

DETAILED DESCRIPTION

The disclosure refers to particular features, including process or method steps. Those of skill in the art understand that the disclosure is not limited to or by the description of embodiments given in the specification. The subject matter of this disclosure is not restricted except only in the spirit of the specification and appended claims.

Those of skill in the art also understand that the terminology used for describing particular embodiments does not limit the scope or breadth of the embodiments of the disclosure. In interpreting the specification and appended claims, all terms should be interpreted in the broadest possible manner consistent with the context of each term. All technical and scientific terms used in the specification and appended claims have the same meaning as commonly understood by one of ordinary skill in the art to which this disclosure belongs unless defined otherwise.

Although the disclosure has been described with respect to certain features, it should be understood that the features and embodiments of the features can be combined with other features and embodiments of those features.

Although the disclosure has been described in detail, it should be understood that various changes, substitutions, and alternations can be made without departing from the principle and scope of the disclosure. Accordingly, the scope of the present disclosure should be determined by the following claims and their appropriate legal equivalents.

As used throughout the disclosure, the singular forms "a," "an," and "the" include plural references unless the context clearly indicates otherwise.

As used throughout the disclosure, the word "about" includes +/−20% of the cited magnitude.

As used throughout the disclosure, the words "comprise," "has," "includes," and all other grammatical variations are each intended to have an open, non-limiting meaning that does not exclude additional elements, components or steps. Embodiments of the present disclosure may suitably "comprise," "consist," or "consist essentially of" the limiting features disclosed, and may be practiced in the absence of a limiting feature not disclosed. For example, it can be recognized by those skilled in the art that certain steps can be combined into a single step.

As used throughout the disclosure, the words "optional" or "optionally" means that the subsequently described event or circumstances can or may not occur. The description includes instances where the event or circumstance occurs and instances where it does not occur.

Where a range of values is provided in the specification or in the appended claims, it is understood that the interval encompasses each intervening value between the upper limit and the lower limit as well as the upper limit and the lower limit. The disclosure encompasses and bounds smaller ranges of the interval subject to any specific exclusion provided.

Where reference is made in the specification and appended claims to a method comprising two or more defined steps, the defined steps can be carried out in any order or simultaneously except where the context excludes that possibility.

As used throughout the disclosure, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present disclosure.

As used throughout the disclosure, spatial terms described the relative position of an object or a group of objects relative to another object or group of objects. The spatial relationships apply along vertical and horizontal axes. Orientation and relational words are for descriptive convenience and are not limiting unless otherwise indicated.

As used throughout the disclosure, the term "low-loss fluid" refers to a fluid where an electromagnetic wave experiences an insignificant decay in amplitude when travelling through the fluid. More specifically, a low-loss fluid is a fluid whose imaginary part of the complex permittivity (at the frequency of the electromagnetic wave) is equal to or less than about 0.01. Non-limiting examples of a low-loss fluid include liquid hydrocarbons. As opposed to the low-loss fluid, a "high-loss fluid" refers to a fluid where an electromagnetic wave experiences a significant decay in amplitude when travelling through the fluid. Non-limiting examples of a high-loss fluid include water and saline water.

As used throughout the disclosure, the term "trace quantity" refers to a magnitude less than 100 parts per million (ppm), alternately less than 1,000 ppm, alternately less than 10,000 or alternately less than 100,000 ppm.

As used throughout the disclosure, the terms "water" or an "aqueous" substance can include, for example, brine, saline water, connate water, surface water, distilled water, carbonated water, sea water, tap water, and combinations of the same.

As used throughout the disclosure, the term "S-parameter" refers to a constituent of a complex scattering matrix that shows reflection or transmission characteristics (including amplitude and phase) in the frequency domain. For example, a two-port device includes four S-parameters. The first subscript number following the S represents the port where the signal emerges. The second subscript number following the S represents the port where the signal is applied. Accordingly, $S_{11}$ represents a measure of a reflection (that is, the reflection coefficient) from the emerging port. Such S-parameters can be measured by a VNA or a reflectometer.

Certain electromagnetic properties obtained from dielectric/microwave measurements include the relative complex permittivity ($\varepsilon = \varepsilon' - i\varepsilon''$) and the relative magnetic permeability ($\mu$). It is known that the relative magnetic permeability is close to 1 for most geomaterials. Accordingly, for most cases, only the relative complex permittivity is measured.

Depending on the nature of the geomaterials, complex permittivity measurement can be broadband or resonant. Broadband measurements, given their reflection/transmission nature, can have relatively greater uncertainty and relatively lesser accuracy for low-loss materials than those of resonant measurements, especially with respect to the low imaginary part of the relative complex permittivity (the imaginary part typically having a magnitude of less than about 0.1). On the other hand, resonant measurements are conducted in one or more discrete frequencies. Resonant measurements can be used for low-loss materials, such as hydrocarbons, to obtain the low imaginary part of the relative complex permittivity with enhanced accuracy and reduced uncertainty.

Depending on the type of fluid, the frequency range, the property of interest, and the required accuracy, permittivity measurements can be broadband and only measure the real part of the complex permittivity (that is, the dielectric constant). For high-loss fluids, such as water or saline water, broadband methods (such as open coaxial probes or parallel plate systems) could also provide a value for the imaginary part of the complex permittivity. Without being bound by any theory, resonant measurements typically fail when using high-loss fluids because the losses of the fluid can be greater than that of the resonating fixture used. In addition, resonance may not occur at all when using high-loss fluids.

Embodiments of the disclosure related to a method for detecting or quantifying, or both, trace quantities of hydrocarbons present in water using microwave measurements. The temperature of a water or brine-based sample including trace quantities of hydrocarbons is reduced below the freezing point of the water or brine-based sample to minimize the contribution of the dielectric constant of water when taking microwave measurements. Subsequently, the solid state sample is transferred to a microwave resonant cavity. Microwaves are transmitted to the sample to obtain certain scattering parameters of the sample. In particular, the reflection coefficient (corresponding to $S_{11}$ of the scattering matrix) is obtained via microwave scattering to determine the complex permittivity of the sample at one or more resonant frequencies.

Using the dielectric/permittivity spectra from hydrocarbons to characterize their content in an aqueous medium requires knowledge of their geochemistry and the geological processes that formed them. Microwave characterization of hydrocarbons presents a faster way to characterize and screen the geochemical properties of a hydrocarbon fluid, such as API gravity (American Petroleum Institute gravity), maturity, and quality. However, as the hydrocarbons have low conductivity, resonant methods can be utilized to obtain accurate readings for both the real and imaginary part of the permittivity. Disclosed here are the uses of multipoint resonant cavities in the analysis of trace quantities of hydrocarbons present in an aqueous medium at one or more temperatures to characterize the hydrocarbon content. Embodiments include methods of characterization of the hydrocarbons using complex permittivity measurements at predetermined temperatures using multipoint resonant cavities. In some embodiments, complex permittivity measurements of trace quantities of hydrocarbons present in an aqueous medium can be obtained at about −30 deg. C. and about 0 deg. C. using one or more multipoint resonant cavities. In some embodiments, the complex permittivity measurements can be obtained at one or more frequencies. In some embodiments, these complex permittivity measurements can be related back to specific components of the hydrocarbons, such as the asphaltene content, the aromatic content, the xylene content, the toluene content, and the heptane content of the hydrocarbons. Certain embodiments of methods of identifying trace quantities of hydrocarbons present in an aqueous medium include obtaining complex permittivity values for different frequencies between 100 MHz and 20 GHz. Certain embodiments of methods of identifying trace quantities of hydrocarbons present in an aqueous medium include obtaining complex permittivity values for nine different frequencies between 170 MHz and 8.6 GHz. For example, the complex permittivity spectra can be related back to the asphaltene content, which is a function of the maturity of the source rock from where the hydrocarbons originated, and also the aromatic content, which is derived due to either thermochemical sulfate reduction or evaporative fractionation. In addition, at frequencies ranging from 2 GHz to 8.6 GHz, the complex permittivity spectra can be correlated with the xylenes and the toluene content of the produced fluids.

Microwave measurements provide values for the relative complex permittivity of a material under test. The complex permittivity is used to characterize important properties of fluids such as density and chemical composition. The relative complex permittivity is given in Equation (1):

$$\varepsilon(f,T,C) = \varepsilon'(f,T,C) - j\varepsilon''(f,T,C) \quad (1)$$

where f is the frequency, T is the temperature, and C is the chemical composition. The imaginary part is given in Equation (2):

$$\varepsilon''(f,T,C) = \varepsilon''_d(f,T,C) + \sigma_{DC}(T,C)/2\pi f \varepsilon_0 \quad (2)$$

where $\sigma_{DC}$ is the direct current (DC) conductivity and $\varepsilon_0$ is the permittivity of vacuum. The first term represents the dielectric losses and the second term represents the conductive losses.

The polarization of a dielectric resulting from permanent dipole moments of molecules in polar fluids decays exponentially. Therefore, the imaginary part of the relative permittivity of polar fluids exhibits a rapid decay from exposure to the low frequencies. The rate of decay decreases depending on the conductivity and composition of the fluid. The decay reaches maxima at certain frequencies, and continues at a decreased pace until a limit value is reached. The frequencies at which the maxima occur are called the relaxation frequencies having unit of inverse seconds ($s^{-1}$). The inverse of the relaxation frequency is defined as the relaxation time. Given the low conductivity of hydrocarbons, hydrocarbons have lesser relaxation frequencies and greater relaxation times with respect to water. In addition, the hydrocarbon component chemistry, which varies with temperature, affects the complex permittivity.

A multipoint resonant cavity can provide microwave measurements at four to five resonant frequencies in a broad spectrum. Using two similarly sized cavities can allow to fill in between the discrete frequencies. Using two cavities of different sizes increases the frequency spectrum range. The larger the cavity, the lower the frequency it provides and vice versa. In some embodiments, a first set of microwave frequencies can range from 100 MHz to 20 GHz. These microwave frequencies can also range from 100 MHz to 10 GHz. In some embodiments, the first set of microwave frequencies can range from 170 MHz to 8.6 GHz. In some embodiments, a second set of two or more microwave frequencies from the low frequency microwave resonant cavity can range from 100 MHz to 2.3 GHz. In some embodiments, the second set of two or more microwave frequencies from the low frequency microwave resonant cavity can range from 170 MHz to 2.3 GHz. A third set of two or more microwave frequencies from the high frequency microwave resonant cavity range from 1.3 GHz to 20 GHz. The third set of two or more microwave frequencies from the high frequency microwave resonant cavity range from 1.3 GHz to 8.6 GHz. In some embodiments, the temperature of the aqueous sample is measured almost immediately (in 5 to 8 seconds) before the temperature increases or decreases. In some embodiments, the aqueous samples are analyzed under a temperature controlled environment. In some embodiments, microwave measurements can be conducted at a temperature ranging between about −50 deg. C. and about 0 deg. C., alternately between about −40 deg. C. and about 0 deg. C., or alternately between about −30 deg. C. and about 0 deg. C. In some embodiments, measuring dielectric measurements at two or more temperatures reduces the fluctuations based on variations in the temperature measurements.

In some embodiments, the frequency range used for measuring the relative complex permittivity of trace quantities of hydrocarbons present in an aqueous medium can range between about 100 MHz and about 150 GHz or alternately between about 15 GHz and about 150 GHz. Without being bound by any theory, the microwave frequency used in the measurement setup can vary depending on the droplet sizes of the hydrocarbons immersed in the aqueous medium.

Microwave cavity measurements can be conducted with either multipoint re-entrant coaxial resonant cavities that give complex permittivity values for a finite number of frequencies or with individual frequency cavities. Frequencies are typically in the GHz range. In some embodiments, the frequencies are set by the cavity geometry (size and shape) and by the type of electromagnetic mode that propagates in such cavity. Embodiments of an experimental setup can include a multipoint re-entrant cavity configured to receive a vial containing a sample. Embodiments of an experimental setup can include a multipoint re-entrant cavity, whose resonance can be modeled by analytical or numerical methods. The cavities can also be cubes or cuboids in shape. In an embodiment, the apparatus is a cylindrical cavity configured to accept a vial containing the liquid hydrocarbon sample and function at frequencies as low as 100 MHz. In an embodiment, the cavity has a coaxial opening in the top that does not extend all the way to the bottom. In some embodiments, the cavity has a removable lid for placing and removing samples, a sample holder, a resonator mechanism for adjusting the resonance frequency of the cavity, an output dielectric response detector, and one or more fastening mechanisms for securely holding the lid to the base during operation. Sources of microwaves are communicatively connected to the cavity, and detectors are provided on the sides of the cavity or as mounted on the cavity lid. The external microwave sources and detectors are controlled by a computer using an appropriate software. Vials containing test samples can be in the form of rectangular solids or cylinders, with the dimensions suitably appropriate to the height and diameter of the cavity. In some embodiments, the cavity has inlet and outlet ports for gas such that the cavity could be pressurized and put under an artificial atmosphere. The experimental setup can include components to adjust the frequency of the microwaves delivered to the sample. The experimental setup can include shielding components to protect the operators from electromagnetic radiation.

Certain embodiments of the cavities are made of aluminum. In an embodiment, the cavity is partially filled with polytetrafluoroethylene compounds to further lower the frequency delivered to the sample. In certain embodiments, the polytetrafluoroethylene compound is Teflon®. In an embodiment, the low frequency cavity has a diameter of about 59.6 millimeters (mm) and a length of about 250 mm. This cavity is configured to hold a vial with an internal diameter of 13 mm. To deliver frequencies of about 100 MHz, the length of the cavity can be increased. In certain embodiments, the cavities can be made of more conductive materials, such as silver, copper, or gold, to minimize the losses suffered at lower frequencies. Certain embodiments include a silver bath in the inner surfaces of a large cavity to capture resonant modes at lower frequencies.

In some embodiments, the high frequency cavity is made of aluminum. Its dimensions can include an internal diameter of about 40 mm and a length of about 97.8 mm. This cavity is configured to hold a vial with an internal diameter of about 8 mm. All cavities are well characterized in the modeling system to achieve accurate values with the inversion algorithm.

Certain embodiments involve the use of a multipoint re-entrant microwave cavity, and not a photonic band gap cavity. In some embodiments, a cavity can be a cylinder with no periodic arrangement of materials having dissimilar permittivity. Unlike other technologies, where different cavities are used for different frequencies, the experimental setup is configured to provide for the multifrequency features and can also include a cavity with an opening in the middle. An example of a multipoint re-entrant microwave cavity is an aluminum multipoint cavity with a quartz vial inserted from the top. Certain embodiments of the methods of measuring the dielectric responses include operating the cavities at very specific temperatures. A method of measuring the dielectric responses includes the steps of reducing the temperature of an aqueous sample such that the aqueous sample is in its solid state, and measuring the temperature of that solid state aqueous sample. If the temperature is steady, dielectric responses of that solid state aqueous sample are collected and analyzed. If the temperature is not steady, certain temperature-controlling means can be used to reach steady temperatures. All samples under evaluation are maintained at about the same temperatures.

The aqueous sample can be open to the atmosphere or in a sealed container. The container can be made of a material where the dielectric properties remain unchanged within the desired temperature range. For example, quartz or sapphire can be used as the container material. Their dielectric properties are constant up to about 1,200° C. In some embodiments, the frequencies range from 100 MHz to 10 GHz.

Certain embodiments of the experimental setup described here can be deployed at the site where the aqueous sample can be collected at production wells. For example, the production fluids can be measured at one or more sampling sites in an oil-productive geologic region. The size of the samples and the design of the cavities can vary to identify the hydrocarbon content in the aqueous sample.

FIG. 1 shows an example experimental setup for identifying trace quantities of hydrocarbons present in an aqueous medium, according to an embodiment of the disclosure. The experimental setup 100 includes two multipoint resonant cavities (Institute of Information and Communication Technologies (ITACA) of the Universitat Politècnica de València, Spain)—a low frequency cavity 102 and a high frequency cavity 104. The low frequency cavity 102 is relatively larger than the high frequency cavity 104. The low frequency cavity 102 is used for relatively lesser frequencies than the high frequency cavity 104. In some embodiments, a single multipoint resonant cavity can be used. The experimental setup further includes a VNA 106 (R&S®ZVA50, Rohde & Schwarz GmbH & Co KG, Munich, Germany). The experimental setup also includes two Gore VNA cables 108, 110, a computer 112 with the cavities software, thermometers 114 (calibrated by National Institute of Standards and Technology services), vials 116, vial holders or stands 118, and a liquid nitrogen bath 120. The VNA 106 is first calibrated using an Agilent Technologies 85052B calibration kit (Agilent Technologies, Inc., Santa Clara, Calif.). The cavities 102, 104 are connected to the VNA 106 with the two VNA cables 108, 110. The measurements can be taken with empty vials on both cavities 102, 104 and measurements during resonant modes can be saved. One or more vials 116 are placed in the liquid nitrogen bath 120 such that the aqueous medium, the hydrocarbon, or the mixture included in the vials 116 transition to solid state. At a target temperature, while the aqueous medium, the hydrocarbon, or the mixture included in the vials 116 are in solid state, the vials 116 can be transferred to their respective cavity and measurements can be taken. The measurements are communicated to and stored by a computer 112 with the cavities software. The mode matching method using the $TE_{0np}$ modes to calculate the generalized impedance matrix, as presented by cavities software, is used to compute the complex permittivity values and quality factors from the resonant frequency values of both the empty vials and vials 116 filled with the aqueous medium, the hydrocarbon, or the mixture. As used throughout the disclosure, a TE mode is a waveguide mode that is dependent upon the transverse electric waves and the integers m, n, and p in the subscript denote the number of half-wave variations in the x, y, and z direction, respectively. Multipoint microwave cavity measurements can be performed to obtain the $S_{11}$ reflection coefficient as a function of frequency (and optionally temperature) via the VNA 106.

From the $S_{11}$ reflection coefficient, the resonant frequencies and quality factor can be identified. In addition, an inversion (described in Alvarez, et al., "Permittivity Spectrum of Low-Loss Liquid and Powder Geomaterials Using Multipoint Reentrant Cavities," IEEE Transactions on Geoscience and Remote Sensing, Vol. 58, pp. 3097-3112, which is incorporated herein by reference in its entirety) can be conducted to convert the S11 reflection coefficient and obtain the relative complex permittivity at one or more resonant frequencies. In order to include the uncertainty from temperature variations, measurements at each cavity can be taken at least at two different temperatures.

Figure 2A:
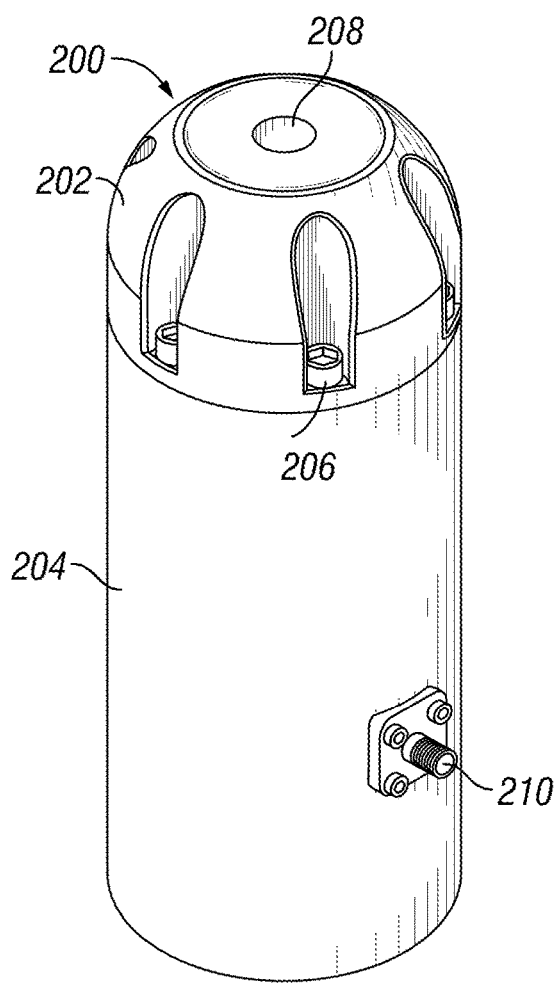
FIG. 2A is a perspective view of a multipoint resonant cavity compatible for microwave measurements for identifying trace quantities of hydrocarbons present in an aqueous medium, according to an embodiment of the disclosure.
Figure 2B:
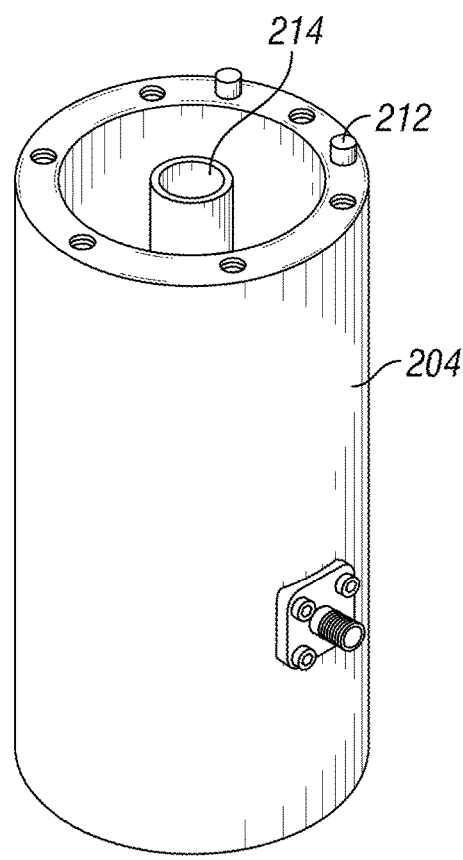
FIG. 2B is a perspective view of a portion of the multipoint resonant cavity compatible for microwave measurements for identifying trace quantities of hydrocarbons present in an aqueous medium, according to an embodiment of the disclosure.
Figure 2C:
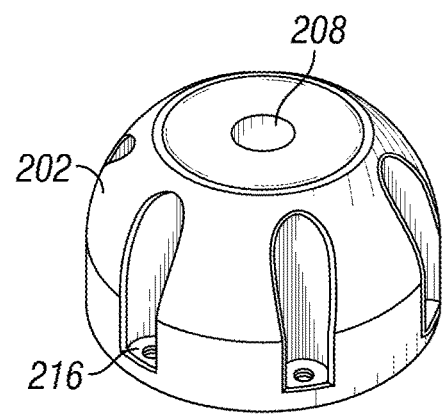
FIG. 2C is a perspective view of a portion of the multipoint resonant cavity compatible for microwave measurements for identifying trace quantities of hydrocarbons present in an aqueous medium, according to an embodiment of the disclosure.

FIGS. 2A-2C show perspective views of a multipoint resonant cavity 200 compatible for microwave measurements for identifying trace quantities of hydrocarbons present in an aqueous medium, according to an embodiment of the disclosure. As shown in FIG. 2A, the cavity 200 is a cylindrical cavity configured to accept a vial containing a sample and function at frequencies as low as 100 MHz. The cavity 200 has two components, a lid 202 and a base 204. The lid 202 and base 204 are secured together by a series of nuts and bolts 206 serving as the fastening mechanism. The lid 202 has a coaxial opening 208 on the top that does not extend all the way to the bottom of the cavity 200. The cavity 200 is also equipped with port 210 that communicatively connects the cavity 200 to the dielectric response detection system. Not shown, but also provided here is a port that communicatively connects the cavity 200 to the source of microwaves. The external microwave sources and dielectric response detectors are controlled by a computer, running appropriate software. FIG. 2B and FIG. 2C are perspective views of the base 204 and the lid 202 respectively, when separated from each other. As shown in FIG. 2B, the base 204 has slots 212 to receive suitable fastening mechanisms, such as bolts. The base 204 also has a station 214 to receive a sample holder such as vial. This station 214 is configured to receive a cylindrical vial. As shown in FIG. 2C, the lid 202 has a coaxial opening 208 on the top and complementary slots 216 to receive suitable fastening mechanisms, such as bolts, to secure the lid 202 to the base 204 via slots 212. One skilled in the art would recognize that microwave-compatible cavities can vary in size and shape depending on the resonant frequencies and materials used for microwave measurement.

Figure 3:
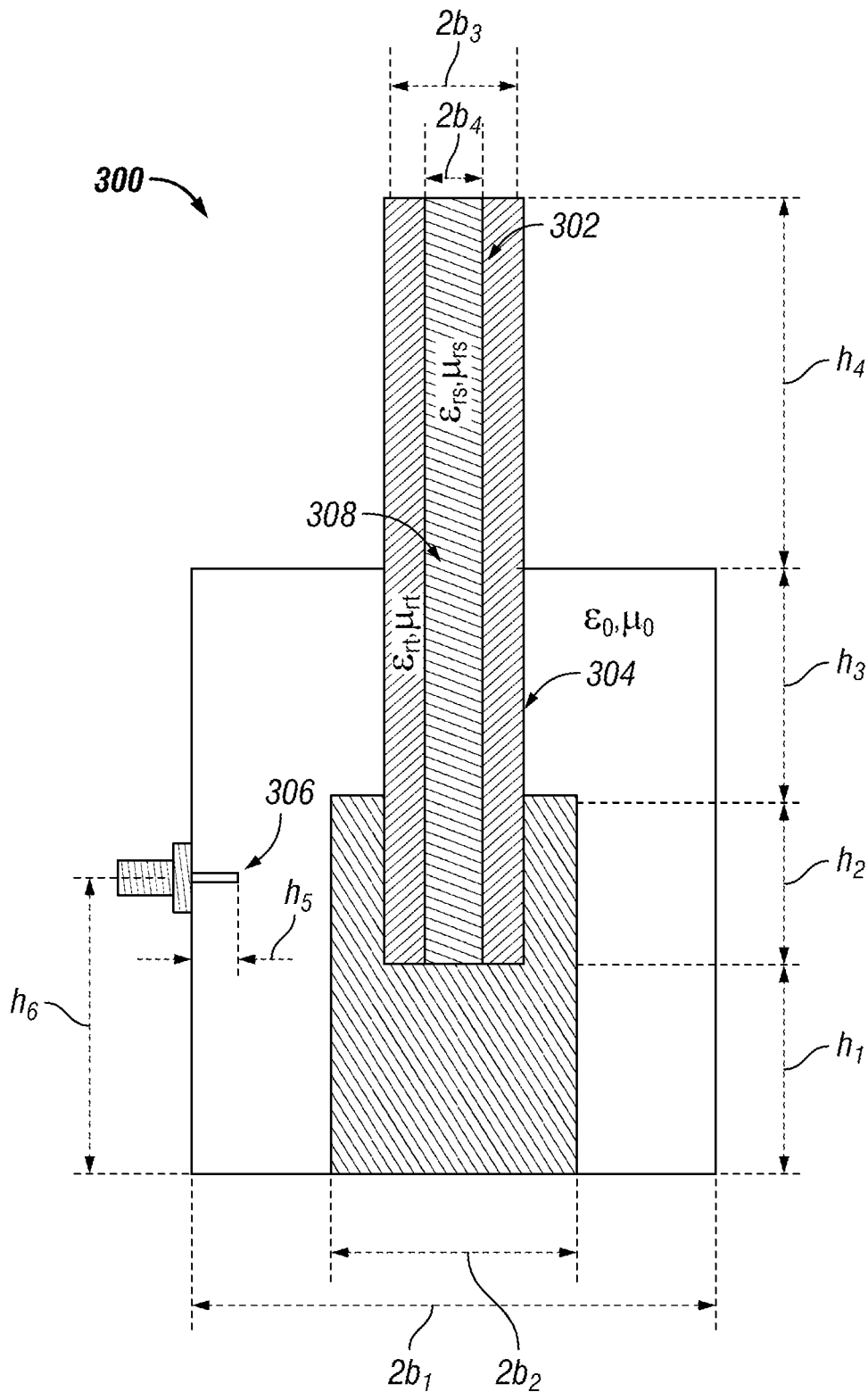
FIG. 3 is a cross-sectional view of a multipoint resonant cavity compatible for microwave measurements for identifying trace quantities of hydrocarbons present in an aqueous medium, according to an embodiment of the disclosure.

FIG. 3 shows a cross-sectional view of a reentrant cavity 300 with a vial 302, according to an embodiment of the disclosure. The black lines and areas are made of metallic material, and the white area represents air. $b_2$ is the coaxial inner radius, $b_1$ the coaxial outer radius, $h_1$ the coaxial length, and $h_3$ the length of circular waveguide. There is one insertion hole on the top of the cavity 300, of length $h_4$, which is below the cutoff frequency to avoid leakage of the electromagnetic energy, and a reentrant hole in the inner coaxial conductor, of length $h_2$, which is also below the cutoff frequency to avoid problems associated with the non-flat bottom of the vial 302.

The cavity 300 is fed by a coaxial line 306 through the lateral wall, at height $h_6$ and penetration of $h_5$. The inserted vial 302 has an external radius of $b_3$, and the inner radius is $b_4$. The permittivity and permeability of the vial 302 are $\varepsilon_{rt}$ and $\mu_{rt}$, respectively, and the permittivity and permeability of the sample 308 inside the vial 302 are $\varepsilon_{rs}$ and $\mu_{rs}$, respectively.

The analysis of the cavity 300 can be done by dividing the whole structure into the smallest and simplest structures that are characterized by their generalized admittance matrices (GAM). The smallest structures are then joined together, enforcing the boundary conditions. Here, the structure is segmented into small structures of 1, 2, 3, and 4 ports, where each port corresponds to a surface and each network is characterized by its GAM. For example, the vertical section represented by $h_1$ includes a 1-port network. The vertical section represented by $h_2$ includes a 3-port network and a 4-port network. The vertical section represented by $h_3$ includes a 3-port network and three 4-port networks. The vertical section represented by $h_4$ includes two 1-port networks. The insertion hole enables the introduction of the sample inside the vial 302 from the upper part and is designed to avoid propagation along the hole. Accordingly, this section does not have any ports because the insertion hole is under the cutoff frequency. There is no reflection from above.

In total, there can exist 42 ports to model the whole resonant geometry. The resonant geometry can be approximated by connecting all the networks of 41 ports, resulting in a 1-port network, and leaving alone 1 port. Here, each 1-port network can be characterized by its own generalized impedance matrix (GIM), which is equivalent to an inverse matrix of GAM.

The resonant frequency can be determined by Equation (3):

$$|\det(\bar{Z}_R + \bar{Z}_L)| = 0 \quad (3)$$

where $\bar{Z}_R$ and $\bar{Z}_L$ represent the GIMs of the two 1-port networks and each are functions of dimension, permittivity, permeability, and frequency. Accordingly, if the dimensional parameters are known and the resonant frequencies and the quality factors can be determined by the VNA or reflectometer, the complex permittivity of the sample can be determined. Equation (3) can be solved using the Nelder-Mead simplex (direct search) method to determine the complex permittivity.

The resonant frequency can exist as a complex number, as shown in Equation (4):

$$\Omega_r = f_r\left(1 - \frac{j}{2Q}\right) \quad (3)$$

where $\Omega_r$ is the complex resonant frequency, $f_r$ is the resonant frequency, and Q is the quality factor of the cavity 300. The real part of the complex resonant frequency provides information regarding the resonant frequency. The imaginary part of the complex resonant frequency provides information regarding the quality factor of the cavity 300. The quality factor corresponds to the losses and is defined as shown in Equation (5):

$$Q = 2\pi f \frac{U_T}{P_L}\bigg|_{f=f_r} \quad (3)$$

where $U_T$ is the total electric and magnetic energies in the cavity and $P_L$ is the total power dissipated by the cavity 300. To reiterate, the resonant frequency and the quality factor can be measured by the VNA or reflectometer.

In an embodiment, one or more example cavities 300 can have dimensions as shown in Table 1. $h_5$ can be optimized to couple enough energy to the cavity 300 to couple resonant modes. The vials 302 can be made of quartz, where the permittivity of quartz can be calculated measuring an empty vial 302.

TABLE 1

| Cavity | Dimension (mm) | | | | | | | | | |
|---|---|---|---|---|---|---|---|---|---|---|
| | $h_1$ | $h_2$ | $h_3$ | $h_4$ | $h_5$ | $h_6$ | $b_1$ | $b_2$ | $b_3$ | $b_4$ |
| 1 | 274 | 20 | 8 | 20 | 2 | 112 | 7 | 7.5 | 6.5 | 5.26 |
| 2 | 29.5 | 20 | 7.7 | 20 | 2 | 36 | 7.03 | 5 | 4.05 | 1.5 |

Figure 4:
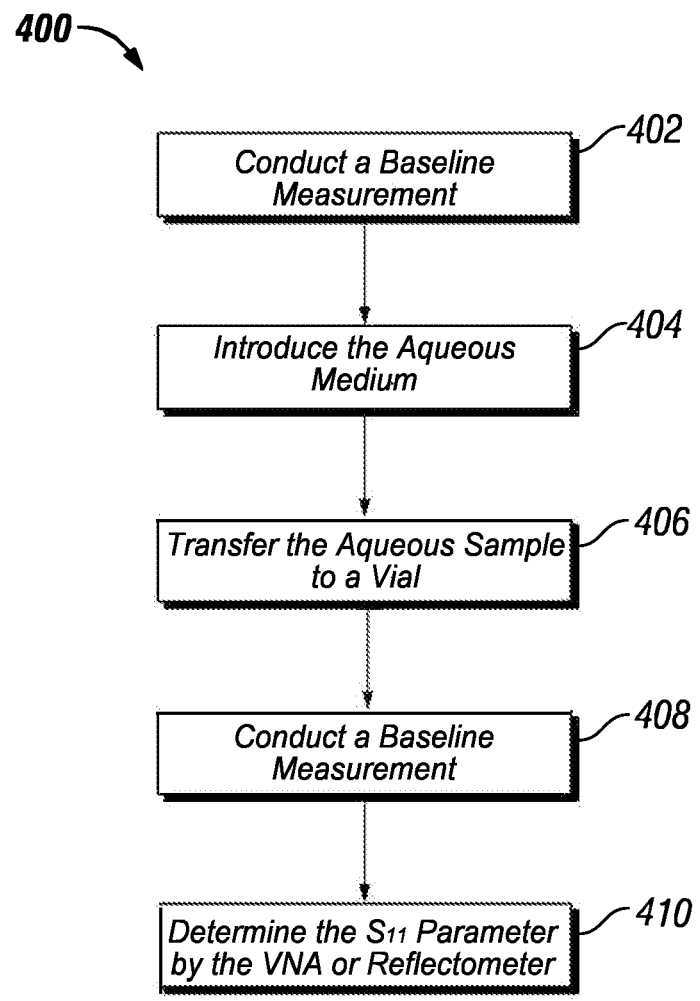
FIG. 4 is a schematic diagram of a process for detecting trace quantities of hydrocarbons in an aqueous medium used for secondary oil recovery, according to an embodiment of the disclosure.

FIG. 4 shows a schematic diagram of a process 400 for detecting trace quantities of hydrocarbons in an aqueous medium used for secondary oil recovery, according to an embodiment of the disclosure.

In step 402, a baseline measurement is conducted to determine the complex permittivity of the aqueous medium (and optionally the hydrocarbon) to be introduced into the subterranean hydrocarbon formation for secondary oil recovery. The baseline measurement can include determining the complex permittivity of the aqueous medium at various frequencies. The baseline measurement can include determining the complex permittivity of the aqueous medium at various salinities. The baseline measurement can include determining the complex permittivity of the aqueous medium at various temperatures, including sub-freezing temperatures. Accordingly, the degree of sensitivity of the measurement can be determined.

In some embodiments, the baseline measurement includes determining the complex permittivity of the hydrocarbon of the subterranean hydrocarbon formation. The baseline measurement can include determining the complex permittivity of the hydrocarbon at various frequencies. The baseline measurement can include determining the complex permittivity of the hydrocarbon at various temperatures. Accordingly, the degree of sensitivity of the measurement can be determined.

In some embodiments, the baseline measurement can include determining the complex permittivity of a mixture of the hydrocarbon of the subterranean hydrocarbon formation and the aqueous medium. The baseline measurement can include determining the complex permittivity of the mixture at various frequencies. The baseline measurement can include determining the complex permittivity of the mixture at various salinities. The salinities can range between about 0.001 M/L and about 1 M/L. The baseline measurement can include determining the complex permittivity of the mixture at various temperatures, including sub-freezing temperatures of the aqueous medium. The baseline measurement can include determining the complex permittivity of the mixture at various trace quantity hydrocarbon concentrations. The hydrocarbon concentrations can range between about 0.0001 wt. % and about 100 wt. %, alternately between about 0.0001 wt. % and about 10 wt. %, or alternately between about 0.001 wt. % and about 1 wt. %. To calibrate and further quantify the hydrocarbon concentration of the aqueous sample including hydrocarbons, after finding the adequate set of cavities in different frequencies, baseline measurements can be conducted by varying the hydrocarbon concentration from 0 wt. %, 0.0001 wt. %, 0.001 wt. %, 0.01 wt. %, 0.1 wt. %, 1 wt. %, 10 wt. % and 100 wt. %. Accordingly, the degree of sensitivity of the measurement can be determined.

In step 404, the aqueous medium (which has undergone a baseline measurement) is introduced into the subterranean hydrocarbon formation through injection wells to displace and produce the hydrocarbons for secondary oil recovery. As secondary oil recovery progresses, the recovery efficiency would reduce over time, and eventually an aqueous sample can be collected at the production wells. The collected aqueous sample can include trace quantities of the hydrocarbons, having a composition similar to the mixture in step 402. Alternately, the aqueous sample can be collected by retrieving a core plug sample of the subterranean hydrocarbon formation.

In step 406, the aqueous sample is transferred to a vial and cooled to a temperature less than the freezing point of the aqueous sample such that at least the aqueous portion of the aqueous sample is in a solid state. Without being bound by any theory, in the dielectric sense, trace quantities of hydrocarbons in an aqueous medium is difficult to identify due to the pervasive dielectric constant (corresponding to the real part of the complex permittivity) of water. In addition, trace quantities of hydrocarbons in saline water (having a conductivity greater than water) are even more difficult to identify. The dielectric contribution of water (including saline water) can be reduced by decreasing the temperature less than the freezing point of the aqueous sample. One skilled in the art would recognize that the freezing point of the aqueous sample may vary due to freezing point depression depending on various salinities in saline water. In this manner, the presence of hydrocarbons can be detected using dielectric spectroscopy utilizing the lower dielectric constant (corresponding to the real part of the complex permittivity) of solid water relative to liquid water. In some embodiments, the temperature can range between about −50 deg. C. and about 0 deg. C., alternately between about −40 deg. C. and about 0 deg. C., or alternately between about −30 deg. C. and about 0 deg. C. The cooling can be conducted by introducing the vial into liquid nitrogen while not submerging the vial in liquid nitrogen. The temperature of the cooled aqueous sample can be monitored by using an infrared temperature sensor. At such temperature range, the dielectric properties do not vary significantly with temperatures, allowing ease of calibration.

In step 408, the solid state aqueous sample is transferred to a cavity (as shown for example in FIGS. 2A-2C and 3) that has a predetermined set of one or more resonant frequencies and connected to the experimental setup (as shown for example in FIG. 1) including a VNA or reflectometer. Microwaves, at a given frequency, are exposed to the solid state aqueous sample through the cavity. A microwave scattering response can be induced due to the hydrocarbon included in the aqueous sample while the dielectric contribution of water is minimized by existing in its solid state. In some embodiments, the temperature of the cavity is not required to be substantially similar to that of the solid state aqueous sample in the vial, as shown in step 406.

In step 410, the $S_{11}$ parameter is determined by the VNA or reflectometer according to the scattering response of the hydrocarbon included in the aqueous sample. This step can be conducted in a manner of seconds and saved to a computer. The $S_{11}$ parameter, which is a frequency response, can be transformed into a time domain parameter by performing an Inverse Fast Fourier Transform (IFFT) and further obtain the resonant frequencies and the quality factors at such resonant frequencies. Once the dimensional parameters are known and the resonant frequencies and the quality factors are determined, the complex permittivity of the sample can be obtained by solving Equation (3). Moreover, the hydrocarbon concentration of the aqueous sample can be quantified by comparing the baseline measurements conducted in step 402 and the aqueous sample measurements conducted in steps 408 and 410.

Examples

This disclosure is illustrated by the following examples, which are presented for illustrative purposes only, and are not intended as limiting the scope of the invention which is defined by the appended claims.

Permittivity measurements were conducted using the experimental setup similar to FIG. 1. In one experiment, a control sample of tap water was placed in a vial and subsequently introduced into a liquid nitrogen bath. Thereafter, the vial was introduced to a multipoint resonant cavity similar to FIGS. 2 and 3 having resonant frequencies at 0.1757 GHz, 0.5247 GHz, 0.8801 GHz, 1.9342 GHz, and 2.287 GHz. Microwave measurements were taken at these frequencies and permittivity values were determined. In another experiment, an aqueous sample, including a mixture of 96 wt. % tap water and 4 wt. % oil (liquid hydrocarbon), was placed in a vial and subsequently introduced into a liquid nitrogen bath. Thereafter, the vial was introduced to the same multipoint resonant cavity. Microwave measurements were taken at the same five frequencies and permittivity values were determined. The results are shown in FIG. 5.

Figure 5:
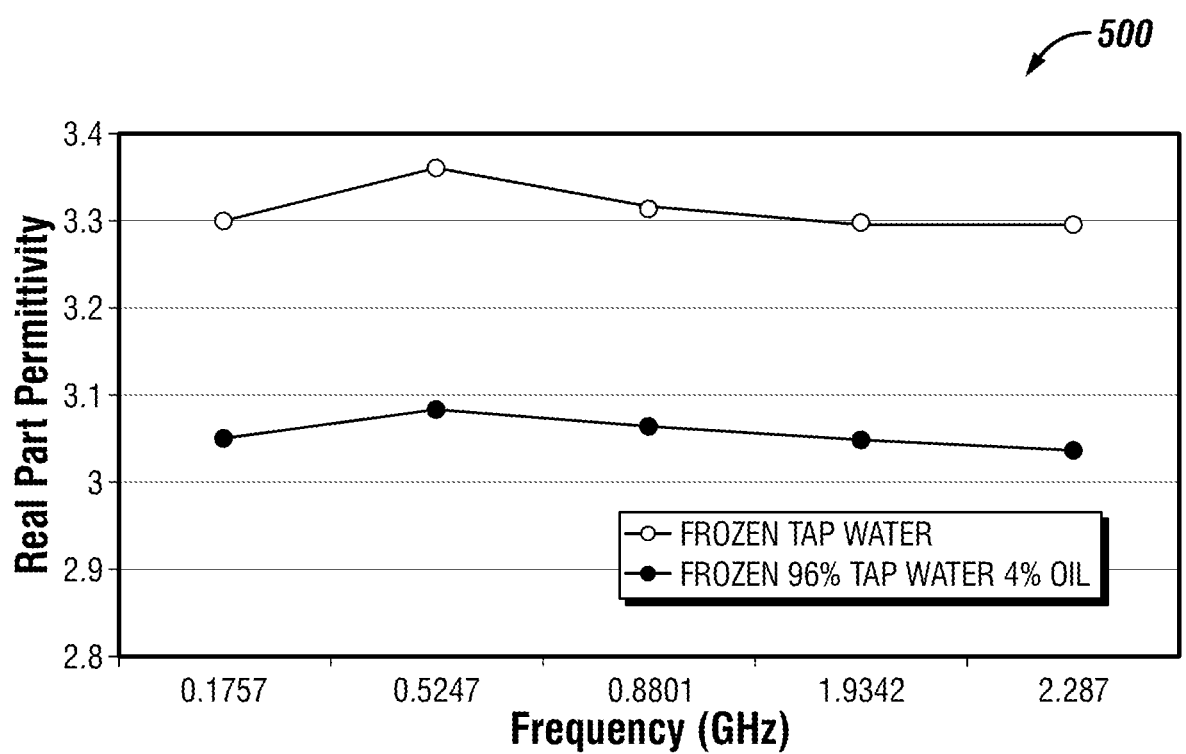
FIG. 5 is a graphical representation showing real part permittivity values of certain samples measured in five different microwave frequencies, according to an embodiment of the disclosure.

FIG. 5 is a graphical representation showing real part permittivity (that is, dielectric constant) values of certain samples measured in five different microwave frequencies, according to an embodiment of the disclosure. The empty circular data points correspond to the real part permittivity of the control sample. The filled circular data points correspond to the real part permittivity of the aqueous sample. As shown in FIG. 5, the real part permittivity of the aqueous sample is generally less than that of the control sample at all five resonant frequencies, due to the presence of hydrocarbons. The results show that microwave measurements of trace hydrocarbons included in the aqueous sample can be conducted by minimizing the dielectric contribution of high-loss fluids via solid state conversion.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method of determining the presence of a hydrocarbon in an aqueous medium used for secondary oil recovery, the method comprising the steps of:

introducing the aqueous medium into a subterranean hydrocarbon formation to displace hydrocarbons;

retrieving an aqueous sample from the aqueous medium introduced into the subterranean hydrocarbon formation;

cooling the aqueous sample such that the aqueous sample is in a solid state;

exposing the aqueous sample to an electromagnetic wave at a microwave frequency such that a scattering response is induced from the hydrocarbon included in the aqueous sample; and determining permittivity of the hydrocarbon based on the scattering response.

2. The method of claim 1, further comprising the step of: identifying hydrocarbon content of the aqueous sample.

3. The method of claim 2, wherein the hydrocarbon content ranges between 0.001 wt. % and 10 wt. %.

4. The method of claim 1, further comprising the step of: obtaining a baseline measurement of the permittivity of the aqueous medium to be introduced into the subterranean hydrocarbon formation.

5. The method of claim 1, wherein the retrieving step is conducted at a production well.

6. The method of claim 1, wherein the aqueous sample has a temperature ranging between 50 deg. C. and 0 deg. C. in the cooling step.

7. The method of claim 1, wherein the exposing step is conducted in a microwave resonant cavity.

8. The method of claim 6, wherein the microwave resonant cavity provides at least four microwave frequencies.

9. The method of claim 1, wherein the microwave frequency ranges between 100 MHz and 150 GHz.

10. The method of claim 1, wherein the aqueous medium has a salinity ranging between 0.001 M/L and 1 M/L.

11. The method of claim 1, wherein the exposing step and the determining step are conducted using a VNA or a reflectometer.

12. The method of claim 1, wherein the determining step includes obtaining an $S_{11}$ reflection coefficient from the scattering response.

* * * * *